(12) United States Patent
Schirmann et al.

(10) Patent No.: US 6,562,311 B1
(45) Date of Patent: May 13, 2003

(54) METHOD FOR PREPARING HYDRAZINE HYDRATE

(75) Inventors: Jean-Pierre Schirmann, Oullins (FR); Paul Bourdauducq, Chaponost (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/744,558

(22) PCT Filed: Jul. 9, 1999

(86) PCT No.: PCT/FR99/01685

§ 371 (c)(1),
(2), (4) Date: Jan. 25, 2001

(87) PCT Pub. No.: WO00/12430

PCT Pub. Date: Mar. 9, 2000

(30) Foreign Application Priority Data

Aug. 26, 1998 (FR) .............................................. 98 10715

(51) Int. Cl.⁷ ......................... C01B 21/16; C07C 45/00; C07C 241/00; C07C 241/02
(52) U.S. Cl. ...................... 423/407; 564/249; 568/403
(58) Field of Search ................................ 568/403, 383; 564/249; 423/407

(56) References Cited

U.S. PATENT DOCUMENTS

| | | | | | |
|---|---|---|---|---|---|
| 3,332,739 A | * | 7/1967 | Needham et al. | ........... | 423/407 |
| 3,981,923 A | * | 9/1976 | Stouthamer et al. | ......... | 252/472 |
| 4,005,179 A | * | 1/1977 | Eichenhofer et al. | ....... | 423/407 |
| 4,075,128 A | * | 2/1978 | Zak | ............................ | 252/475 |
| 4,233,242 A | * | 11/1980 | Nagato et al. | ............... | 564/249 |
| 4,562,296 A | * | 12/1985 | Hargis | ......................... | 568/403 |
| 4,657,751 A | | 4/1987 | Alicot et al. | | |
| 5,103,066 A | * | 4/1992 | Dessau | ........................ | 568/406 |
| 5,239,119 A | * | 8/1993 | Schirmann et al. | ......... | 564/249 |
| 5,252,309 A | | 10/1993 | Krempf et al. | | |
| 5,986,134 A | * | 11/1999 | Kuriyama et al. | .......... | 423/407 |

FOREIGN PATENT DOCUMENTS

| | | |
|---|---|---|
| AU | 55766/90 | 11/1990 |
| EP | 0758642 A | 2/1997 |

* cited by examiner

Primary Examiner—Wayne A. Langel
(74) Attorney, Agent, or Firm—Pennie & Edmonds LLP

(57) ABSTRACT

The invention concerns a method for preparing methyl ethyl ketone azine which consists in: (a) reacting ammonia, hydrogen peroxide and methyl ethyl ketone in the presence of a working solution to form an azine; (b) separating the working solution and the azine possibly containing methyl ethyl ketone which has not reacted and butanol-2; (c) recycling the working solution to step (a) after optional treatment; (d) separating the methyl ethyl ketone and the butanol-2 from the azine. The butanol-2 of the flow in step (d) is either purged or dehydrogenated in MEK and recycled at step (a).

9 Claims, No Drawings

METHOD FOR PREPARING HYDRAZINE HYDRATE

The present invention relates to a process for the preparation of hydrazine hydrate. The present invention relates more specifically to an improved process for the manufacture of hydrazine hydrate from methyl ethyl ketone azine obtained by oxidation of ammonia with hydrogen peroxide in the presence of a coreactant or of a catalyst.

The industrial production of hydrazine hydrate is carried out according to the Raschig, Bayer or hydrogen peroxide processes.

In the Raschig process, ammonia is oxidized with a hypochlorite in order to obtain a dilute hydrazine hydrate solution, which solution subsequently has to be concentrated by distillation. This process is not very selective, has a low yield and is highly polluting, and is virtually no longer used.

The Bayer process is an alternative form of the Raschig process which consists in shifting a chemical equilibrium by trapping, using acetone, the hydrazine formed in the azine form $(CH_3)_2C=N-N=C-(CH_3)_2$. The azine is subsequently isolated and then hydrolysed to hydrazine hydrate. The yields are improved but there is no improvement with respect to the discharges to the environment.

The process with hydrogen peroxide consists in oxidizing a mixture of ammonia and a ketone with hydrogen peroxide in the presence of a means for activating the hydrogen peroxide in order to directly form the azine, which it is sufficient subsequently to hydrolyse to hydrazine hydrate. The yields are high and the process is not polluting. This process with hydrogen peroxide is used by the Applicant Company and is disclosed in numerous patents, for example U.S. Pat. No. 3,972,878, U.S. Pat. No. 3,972,876, U.S. Pat. No. 3,948,902 and U.S. Pat. No. 4,093,656.

The hydrolysis of an azine to hydrazine hydrate is disclosed in U.S. Pat. No. 4,724,133 (Schirmann et al.), U.S. Pat. No. 4,725,421 (Schirmann et al.) and GB 1,164,460. This hydrolysis is carried out in a distillation column which is fed with water and azine. The ketone is recovered at the top and the hydrazine hydrate at the bottom.

EP 70,155 also discloses another hydrogen peroxide process.

These processes are also described in Ullmann's Encyclopaedia of Industrial Chemistry (1989), vol. A 13, pages 182–183 and the references included.

In hydrogen peroxide processes, ammonia is oxidized with hydrogen peroxide in the presence of a ketone and of a means for activating the hydrogen peroxide according to the following overall reaction, an azine being formed:

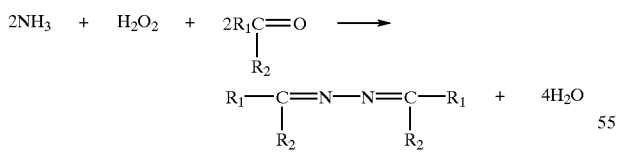

The activation means can be a nitrile, an amide, a carboxylic acid or a selenium, antimony or arsenic derivative. The azine is then hydrolysed to hydrazine and the regenerated ketone is recycled according to the following reaction:

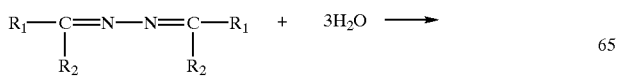

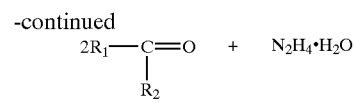

This hydrolysis is carried out in a distillation column. The ketone is recovered at the top and the hydrazine hydrate at the bottom.

The formation is observed, in all processes using MEK (methyl ethyl ketone) and hydrogen peroxide, of impurities derived from MEK and resulting from side reactions. In particular, the formation of 2-butanol is observed, which product originates from a reduction of methyl ethyl ketone by a hydrazine derivative, which can be according to a process of the diimine type

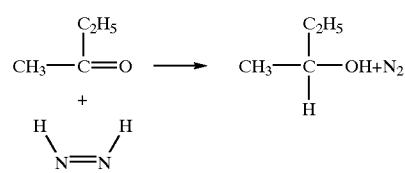

This formation of 2-butanol has already been disclosed in European Patent Application EP 758,642 A2 and it is indicated that the azine yield is sizeably reduced if the 2-butanol is allowed to accumulate and if its ratio with respect to the methyl ethyl ketone exceeds 0.05 mol per mole of MEK and that it was necessary to separate the 2-butanol by distillation and then to bleed it off.

The Applicant Company has discovered that it is possible to dehydrogenate 2-butanol to MEK and to reintroduce it into the process.

A first advantage is that there is a saving of MEK. Another advantage is that it is not necessary to bleed off a stream which is rich in 2-butanol or composed essentially of 2-butanol. Patent EP 758,642 discloses that the 2-butanol is bled off after it has been separated from the MEK and the water. In this prior art, it is necessary to obtain a stream which is fairly rich in 2-butanol in order to avoid also bleeding off MEK. To obtain a stream which is rich in 2-butanol, a separation operation, such as a distillation, is necessary. This concentrating of 2-butanol is no longer necessary in the present invention or does not need to be pushed as far as in the prior art. This is because the stream comprising the 2-butanol can comprise MEK; this mixture of MEK and of 2-butanol is converted, using a dehydrogenating catalyst, to a stream of MEK, which is recycled in the process.

According to a first form, the present invention is a process for the preparation of methyl ethyl ketone azine, in which:

(a) ammonia, hydrogen peroxide and methyl ethyl ketone are reacted in the presence of a working solution, in order to form an azine;

(b) the working solution and the azine, optionally comprising unreacted methyl ethyl ketone and 2-butanol, are separated;

(c) the working solution is recycled to the stage (a) after an optional treatment;

(d) the methyl ethyl ketone and the 2-butanol are separated from the azine;

(e) all or part of the stream from the stage (d) comprising methyl ethyl ketone and 2-butanol is treated in order to dehydrogenate all or part of the 2-butanol to methyl ethyl ketone and the whole (treated and untreated) is recycled to the stage (a).

In a preferred embodiment of this first form of the invention, the azine collected in the stage (d) is hydrolysed in a stage (f) in order to obtain hydrazine hydrate and the regenerated methyl ethyl ketone is recycled to the stage (a).

Use is made, in Application EP 758,642, of a means for activating hydrogen peroxide composed of a mixture of cacodylic acid (dimethylarsinic acid) and of ammonium acetate or of ammonium propionate. If the amount of 2-butanol is 0.05 mol per mole of MEK, the azine yield with respect to the hydrogen peroxide is 84%. If the amount of 2-butanol is 0.1 mol per mole of MEK, the azine yield with respect to the hydrogen peroxide falls to 60%. The Applicant Company has just discovered that this effect of the butanol is not general and is related to the nature of the system for activating the hydrogen peroxide.

Thus, the Applicant Company has just discovered that, in contrast to what is disclosed in Patent Application EP 758,642, the 2-butanol does not have an effect on the yield if the system for activating the hydrogen peroxide is composed of a mixture of a carboxylic acid amide and of the corresponding ammonium salt (for example, acetamide and ammonium acetate) in aqueous solution and if there is no derivative comprising arsenic. It is therefore necessary to distinguish activation systems for which the butanol has an effect on the azine yield, that is to say that the azine yield with respect to the hydrogen peroxide falls when the 2-butanol/MEK ratio increases or is greater than a certain threshold, and activation systems for which the butanol has no effect on the azine yield.

The Applicant Company has also discovered that, in processes using an activation system for which the butanol is without effect on the yield, it is useful to bleed off this butanol because, although it does not cause the reaction yield to fall as described above, it takes the place of the MEK and the production falls due to lack of reactant. The 2-butanol is therefore bled off so that its molar proportion with respect to the MEK is, for example, from 5 to 15 mol per 100 mol of MEK. This purification of the MEK is therefore easy because this content is not excessively low and is easy to achieve and fluctuations with regard to the level of 2-butanol in the MEK can be accepted without there being variations with regard to the yield of the reaction for the synthesis of azines.

According to a second form, the present invention is therefore a process for the preparation of methyl ethyl ketone azine, in which:

(a) ammonia, hydrogen peroxide and methyl ethyl ketone are reacted in the presence of a working solution, in order to form an azine;

(b) the working solution and the azine, optionally comprising unreacted methyl ethyl ketone and 2-butanol, are separated (c) the working solution is recycled to the stage (a) after an optional treatment;

(d) the methyl ethyl ketone and the 2-butanol are separated from the azine (e) part of the 2-butanol is bled off from the stream from the stage (d), so as to maintain the 2-butanol/MEK molar ratio between 0.05 and 0.15 at the inlet of the stage (a).

In a preferred embodiment of this second form, the azine collected in the stage (d) is hydrolysed in a stage (f) in order to obtain hydrazine hydrate and the regenerated methyl ethyl ketone is recycled to the stage (a).

As regards the first form of the invention, a description is given hereinbelow of the implementational details.

Stage (a)

The hydrogen peroxide can be used in the usual commercial form, for example as an aqueous solution comprising between 30 and 90% by weight of $H_2O_2$. One or more conventional stabilizers for peroxide solutions can advantageously be added, for example phosphoric acid, pyrophosphoric acid, citric acid, nitrilotriacetic acid, ethylenediaminetetraacetic acid or the ammonium or alkali metal salts of these acids. The amount to be used is advantageously between 10 and 1000 ppm and preferably between 50 and 250 ppm of the combined reactants and working solution at the reactor inlet. The ammonia can be anhydrous or in aqueous solution. The working solution comprises a means for activating the hydrogen peroxide, that is to say a product such that the azine can be produced from ammonia, hydrogen peroxide and methyl ethyl ketone.

This activator can be chosen from organic or inorganic oxyacids, their ammonium salts and generally their derivatives : anhydrides, esters, amides, nitrites, acyl peroxides, or their mixtures. Use is advantageously made of amides, ammonium salts and nitrites.

Mention may be made, by way of examples, of (i) amides of carboxylic acids of formula $R_5COOH$, in which $R_5$ is hydrogen, a linear alkyl radical having from 1 to 20 carbon atoms, a branched or cyclic alkyl radical having from 3 to 12 carbon atoms or a phenyl radical which can be substituted, or (ii) amides of polycarboxylic acids of formula $R_6(COOH)_n$, in which $R_6$ represents an alkylene radical having from 1 to 10 carbon atoms and n has the value 2 or $R_6$ can be a single bond. The $R_5$ and $R_6$ radicals can be substituted by halogens or OH, $NO_2$ or methoxy groups. Mention may also be made of the amides of the organic acids of arsenic. The organic acids of arsenic are, for example, dimethylarsinic acid, phenylarsonic acid and cacodylic acid.

The preferred amides are formamide, acetamide, monochloroacetamide and propionamide.

Use is advantageously made, among ammonium salts, of the salts of hydracids, of inorganic oxyacids, of arylsulphonic acids, of $R_5COOH$ acids or of $R_6(COOH)_n$ acids, $R_5$, $R_6$ and n being defined above, or of the organic acids of arsenic.

The preferred ammonium salts are the formate, acetate, monochloroacetate, propionate, phenylarsonate and cacodylate. Mention may advantageously be made, among the nitrites, of the products of formula $R_7(CN)_n$, it being possible for n to vary from 1 to 5, depending on the valency of $R_7$, and $R_7$ being a polyvalent radical derived from a cyclic or non-cyclic alkyl having from 1 to 12 carbon atoms or from benzene or pyridine. $R_7$ can be substituted by groups which are not oxidized in the reactor of the stage a, for example halogens or carboxyl, carboxylic ester, nitro, amine, hydroxyl or sulphonic acid groups.

The preferred nitrites are acetonitrile and propionitrile.

The working solution is formed by dissolving one or more products chosen from organic or inorganic oxyacids, their ammonium salts and generally their derivatives: anhydrides, esters, amides, nitrites, acyl peroxides, or their mixtures. Use is advantageously made of the preceding amides, ammonium salts or nitrites.

This solution can be aqueous or based on an alcohol or on a mixture of alcohol and water. Use is advantageously made, among the alcohols, of saturated aliphatic alcohols having from 1 to 6 carbon atoms and preferably 1 or 2 carbon atoms.

Use is also advantageously made of diols and more particularly of diols having from 2 to 5 carbon atoms.

Mention may be made, for example, of glycol, propylene glycol, 1,3-propanediol, 1,3- and 1,4-butane-diol and 1,5-pentanediol.

According to another form of the invention, the working solution can be an alcoholic solution of an organic acid of arsenic and is disclosed in Patent EP 70,155, the contents of which are incorporated in the present application. The working solution can also be an aqueous solution of an amide of a weak acid and of the ammonium salt corresponding to this acid, such as disclosed in Patent EP 487,160.

These amides of weak acids are derived from the corresponding carboxylic acids which have a dissociation constant of less than $5 \times 10^{-5}$, that is to say acids which have a pK of greater than 4.3 in aqueous solution at 25° C.

For the polycarboxylic acids, these are the acids for which the constant of the first ionization is less than $5 \times 10^{-5}$.

Mention may be made, by way of examples, of the carboxylic acids of formula $R_8COOH$, in which $R_8$ is a linear alkyl radical having from 1 to 20 carbon atoms or a branched or cyclic alkyl radical having from 3 to 12 carbon atoms or a phenyl radical which can be substituted, or of polycarboxylic acids of formula $R_9(COOH)_n$, in which $R_9$ represents an alkylene radical having from 1 to 10 carbon atoms and n has the value 2 or $R_9$ can be a single bond. The $R_8$ and $R_9$ radicals can be substituted by halogens or OH, $NO_2$ or methoxy groups. Use is preferably made of acetamide, propionamide, n-butyramide or isobutyramide.

The ammonium salt corresponding to acetamide is ammonium acetate.

It would not be departing from the scope of the invention to form the ammonium salt in situ, that is to say to use the corresponding carboxylic acid which gives the ammonium salt by reaction with ammonia.

The proportions of the amide and of the corresponding ammonium salt can vary within wide limits. Use is usually made of 1 to 25 parts of the ammonium salt per 5 parts of amide and preferably 2 to 10.

The reactants can be used in stoichiometric amounts. However, use is made, per mole of hydrogen peroxide, of 0.2 to 5 mol and preferably of 1.5 to 4 mol of methyl ethyl ketone and of 0.1 to 10 mol and preferably of 1.5 to 4 mol of ammonia. The amount of working solution is between 0.1 and 1 kg per mole of hydrogen peroxide. This amount depends on its quality, that is to say on its catalytic strength or its activity which makes it possible to convert the reactants to azine. The proportions of the reactants laid down above make it possible to obtain complete conversion of the hydrogen peroxide and a production of azine corresponding to more than 50%, and which can reach 90%, of the hydrogen peroxide charged.

The hydrogen peroxide, ammonia and methyl ethyl ketone can be brought into contact with the working solution in any way.

The reaction is advantageously carried out in a homogeneous medium or in a medium which provides at least sufficient solubilization of the reactants for it to be possible to obtain the azine. The reaction can be carried out in a very wide temperature range, for example between 0 and 100° C., and is advantageously carried out between 30 and 70° C. Although it is possible to carry out the reaction at any pressure, it is simpler to be at atmospheric pressure. However, the pressure can rise up to approximately 10 bar if this is necessary in order to preferably maintain the reaction of the stage a in the liquid phase.

The reactants can be introduced simultaneously or separately and in any order into the working solution. It is possible to use all kinds of reactors, stirred or nonstirred, or even simple tanks, which can be arranged in parallel or in series, cocurrentwise or countercurrentwise, or any combination of these possibilities.

Stage (b)

Known means, such as liquid-liquid extraction, distillation, separation by settling or any combination of these possibilities, are used to separate (i) the azine, the excess methyl ethyl ketone and the 2-butanol from (ii) the working solution.

Methyl ethyl ketone is advantageous because its azine is insoluble in the working solution.

The working solution can be treated in the stage (c).

The stages (a), (b) and (c) are disclosed, for example, in Patents EP 399,866 and EP 518,728, the contents of which are incorporated in the present application.

Stage (d)

The methyl ethyl ketone and the 2-butanol are separated from the azine. The operation can be carried out by distillation at atmospheric pressure or under reduced pressure. The methyl ethyl ketone azine (also denoted by mekazine) is collected at the bottom of the distillation column.

Stage (e)

The stream comprising the methyl ethyl ketone and the 2-butanol can be treated in whole or in part in order to dehydrogenate the 2-butanol. It is possible, for example, to treat the entire stream with a low degree of conversion to methyl ethyl ketone or to treat a part with a higher, indeed even total, conversion to methyl ethyl ketone and then the streams are mixed and recycled to the stage (a) or recycled separately to the stage (a). The essence of this stage is the amount of 2-butanol which has to be dehydrogenated to methyl ethyl ketone. This dehydrogenation is known per se. It is disclosed in Ullmann's Encyclopaedia of Industrial Chemistry, vol. A4, pp. 477–478. It is carried out between 180 and 400° C. and between 0.1 and 0.6 MPa over catalysts based on zinc oxide, on chromium oxide, on copper oxide, on alumina or even on platinum. The amount of 2-butanol which is dehydrogenated to methyl ethyl ketone depends on the amount which is formed in the reactor of the stage (a). The content of 2-butanol which is accepted at the inlet of the stage (a) depends on the system for activating the hydrogen peroxide which is used in the stage (a).

It was explained above that catalysts can operate in the presence of more or less 2-butanol.

The amount of 2-butanol at the inlet of the stage (a) is adjusted by more or less forcing the dehydrogenation in order to dehydrogenate a more or less greater amount and by achieving a more or less higher concentration.

Activation systems comprising arsenic are not generally sensitive to 2-butanol. However, in the face of the variety of systems available, it is difficult to make an a priori classification.

Systems for activation of hydrogen peroxide can be easily classified in order to find out which are sensitive to 2-butanol and which are not.

It is sufficient to proceed as in the device disclosed in Comparative Example 1 of Patent EP 758,642. It is quickly discovered from what 2-butanol/MEK ratio the reaction for the synthesis of azine becomes sensitive to the butanol.

As regards the activation systems which are sensitive to 2-butanol, such as, for example, those which are exemplified in EP 758,642, the amount of 2-butanol at the inlet of the stage (a) will be adjusted to a 2-butanol/MEK molar ratio which is less than 0.05.

As regards the systems which are insensitive to 2-butanol, such as, for example, those not comprising arsenic and/or those disclosed in EP 487,160, values of the butanol/MEK ratio at the inlet of the stage (a) of up to 0.15 and advantageously between 0.05 and 0.15 can be accepted. It has been seen above that higher values are without advantage because, although there is not a harmful effect on the reaction yield, there is a loss of productivity due to insufficient reactants.

The stage (f) is carried out, for example, in a plate or packed column of distillation column type which is fed with the azine originating from the stage (b) and water. The following are obtained: (i) at the top, methyl ethyl ketone in the form of an azeotrope with water, and (ii) at the bottom, an aqueous hydrazine hydrate solution.

The hydrolysis of azines is known. For example, E. C. Gilbert, in an article in the Journal of the American Chemical Society, vol. 51, pages 3397–3409 (1929), describes equilibrium reactions for the formation of azine and the hydrolysis reactions of the latter and provides the thermodynamic parameters of the system in the case of water-soluble azines. For example, the hydrolysis of acetone azine is disclosed in U.S. Pat. No. 4,724,133. As regards azines which are insoluble in aqueous solutions (for example, methyl ethyl ketone azine

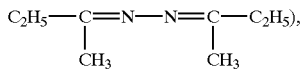

the hydrolysis has to be carried out in a reactive column, such that, by continuously separating the methyl ethyl ketone at the distillation column top and the hydrazine hydrate at the column bottom, complete hydrolysis can be achieved. Of course, this system works best when the operation is carried out continuously, as disclosed in French Patent 1,315,348, British Patent 1,211,547 or U.S. Pat. No. 4,725,421.

In all these patents, the reaction is carried out in a packed distillation column or better still a plate distillation column operating under a pressure of 2 to 25 bar with a bottom temperature of 150° C. to 200° C.

When the operation is carried out with pure azine, that is to say obtained from hydrazine hydrate and methyl ethyl ketone, for example, it is actually found, by operating according to these patents, that dilute hydrazine hydrate solutions are obtained with a good yield.

In this column, the azine is hydrolysed and the hydrazine hydrate is separated from the methyl ethyl ketone. These conditions are known. A person skilled in the art easily determines the number of plates or the packing height, as well as the points for feeding with azine and with water. Solutions comprising 30 or even up to 45% by weight of hydrazine hydrate are obtained at the bottom. This molar ratio of water to azine in feeding this column is at least greater than stoichiometry and advantageously between 5 and 8. The column bottom is between 150 and 200° C., preferably 175 to 190° C. The pressure depends on the boiling temperature of the azine, water and the reactant carrying a carbonyl group. Such a hydrolysis is disclosed in U.S. Pat. No. 4,725,721.

As regards the second form of the invention, the details for the implementation of the stages (a), (b), (c) and (d) are identical to that which has been described above for the first form of the invention, except for the activation system.

This second form very obviously relates to the activation systems for which the 2-butanol is without influence. These systems and the criterion for choice have been described above. The system for activating the hydrogen peroxide advantageously does not comprise arsenic. It is preferably an aqueous solution of an amide of a weak acid and of the corresponding ammonium salt, as described above.

Bleeding off 2-butanol from the stage (e) serves to prevent its accumulation. Since this 2-butanol is not dehydrogenated in order to recycle it in the stage (a), it is preferable to bleed off a stream of 2-butanol which is as pure as possible in order to avoid losing other products, in particular MEK.

EXAMPLE 1

Not in Accordance with the Invention 240 g of water (13.3 mol), 118 g of ammonium propionate (1.3 mol), 40 g of cacodylic acid (0.29 mol) and 2 cm$^3$ of Dequest 2066 stabilizer (sodium salt of diethylenediaminepenta(methylenephosphonic acid) as a 25% aqueous solution), sold by the Company Monsanto, are charged to a reactor. This mixture is brought to 55° C. and then gaseous ammonia is introduced until saturation is reached. 38.9 g of 70% hydrogen peroxide (0.8 mol) are then added over one hour, as well as 144 g of methyl ethyl ketone comprising 2 mol % of 2-butanol (2 mol). The mixture is kept stirred for a further two hours at 55° C. while continuing to introduce gaseous ammonia. It is then allowed to cool. The organic and aqueous phases are separated and are analysed. It is found that the conversion of the hydrogen peroxide is 65.4% and that the azine yield is 45.8%.

EXAMPLE 2

Not in Accordance with the Invention

Example 1 is repeated but the ammonium propionate is replaced with 100 g of ammonium acetate (1.3 mol) and the reaction is allowed to last for 7 hours at 55° C. The conversion of the hydrogen peroxide is 79.3% and the methyl ethyl ketone azine yield is 54%.

EXAMPLE 3

Not in Accordance with the Invention

Example 2 is repeated using methyl ethyl ketone comprising 10 mol % of 2-butanol. The conversion of the hydrogen peroxide is 79.5%, whereas the azine yield falls to 39.8%.

EXAMPLE 4

In Accordance with the Invention 180 g of water (10 mol), 77 g of ammonium acetate (1 mol), 177 g of acetamide (3 mol), 144 g of methyl ethyl ketone (2 mol) and 2 cm$^3$ of Dequest 2066 stabilizer (sodium salt of diethylenediaminepenta-(methylenephosphonic acid) as a 25% aqueous solution), sold by the Company Monsanto, are charged to a reactor. This mixture is brought to 50° C. and is then saturated with ammonia. 48.5 g of 70% hydrogen peroxide (1 mol) are then added over a period of 1 hour. Introduction of gaseous ammonia is continued, so as to keep the medium saturated. Reaction is allowed to take place for 7 hours at 50° C. After cooling to ambient temperature, the aqueous and organic phases are separated. Analysis is carried out and it is found that the H$_2$O$_2$ conversion is 98% for an azine yield of 81%.

EXAMPLE 5

In Accordance with the Invention

Example 4 is repeated but using methyl ethyl ketone comprising 10 mol % of 2-butanol. The conversion of the hydrogen peroxide is 99% and the azine yield is 81.9%.

What is claimed is:

1. A process for the preparation of methyl ethyl ketone azine, comprising the following stages of:
   a) reacting ammonia, hydrogen peroxide, and methyl ethyl ketone in a working solution to form azine;
   b) separating the azine, byproduct 2-butanol, and unreacted methyl ethyl ketone from the working solution;
   c) recycling the working solution to stage (a);
   d) separating the azine from the 2-butanol, and unreacted methyl ethyl ketone;
   e) dehydrogenating at least a part of the 2-butanol obtained in stage (d) to form methyl ethyl ketone; and
   f) recycling the methyl ethyl ketone obtained in stage (e), unreacted 2-butanol in stage (e), and methyl ethyl ketone obtained in stage (d) mixture to stage (a),
      wherein the 2-butanol/methyl ethyl ketone ratio is between 0.05 and 0.15.

2. The process of claim 1, wherein the working solution comprises an activator which is not cacodylic acid.

3. The process of claim 1, wherein the activator is chosen from a group consisting of amides, ammonium salts and nitriles.

4. The process of claim 1, wherein the working solution is an aqueous solution of an amide of a weak acid and of a corresponding ammonium salt.

5. A process for the preparation of methyl ethyl ketone azine, comprising the following stages of:
   a) reacting ammonia, hydrogen peroxide, and methyl ethyl ketone in a working solution to form azine;
   b) separating the azine, byproduct 2-butanol, and unreacted methyl ethyl ketone from the working solution;
   c) recycling the working solution to stage (a);
   d) separating the azine from the 2-butanol, and unreacted methyl ethyl ketone;
   e) bleeding off at least a part of the 2-butanol obtained in stage (d); and
   f) recycling 2-butanol left after stage (e) and methyl ethyl ketone obtained in stage d) to stage (a),
      wherein the 2-butanol/methyl ethyl ketone ratio is between 0.05 and 0.15.

6. The process of claim 5, wherein the working solution comprises an activator which is not cacodylic acid.

7. The process of claim 6, wherein the activator is chosen from a group consisting of amides, ammonium salts and nitriles.

8. The process of claim 5, wherein the working solution is an aqueous solution of an amide of a weak acid and of a corresponding ammonium salt.

9. A process for the preparation of hydrazine hydrate, comprising the process of claim 1 or 5 and the following stages:
   g) hydrolyzing the azine collected in stage (d) to obtain hydrazine hydrate and methyl ethyl ketone; and
   h) recycling the methyl ethyl ketone obtained in stage (g) to stage (a).

* * * * *